(12) United States Patent
Köppel

(10) Patent No.: US 11,786,398 B2
(45) Date of Patent: Oct. 17, 2023

(54) STERILE VENTURI ASPIRATION

(71) Applicant: THIS AG, Heerbrugg (CH)

(72) Inventor: Thomas Köppel, Widnau (CH)

(73) Assignee: THIS AG, Heerbrugg (CH)

( * ) Notice: Subject to any disclaimer, the term of this patent is extended or adjusted under 35 U.S.C. 154(b) by 851 days.

(21) Appl. No.: 16/347,512

(22) PCT Filed: Nov. 2, 2017

(86) PCT No.: PCT/EP2017/078068
§ 371 (c)(1),
(2) Date: May 3, 2019

(87) PCT Pub. No.: WO2018/083181
PCT Pub. Date: May 11, 2018

(65) Prior Publication Data
US 2020/0054802 A1    Feb. 20, 2020

(30) Foreign Application Priority Data
Nov. 3, 2016 (EP) ..................... 16196998

(51) Int. Cl.
*A61F 9/007* (2006.01)
*A61M 1/00* (2006.01)

(52) U.S. Cl.
CPC .......... *A61F 9/00736* (2013.01); *A61M 1/80* (2021.05); *A61F 9/00781* (2013.01); *A61M 1/77* (2021.05);
(Continued)

(58) Field of Classification Search
CPC ............ A61F 9/00736; A61F 9/00781; A61M 2205/12; A61M 2205/128;
(Continued)

(56) References Cited

U.S. PATENT DOCUMENTS 3,254,845 A    6/1966 Schlosser
4,722,366 A *  2/1988 Maaskamp .......... A61M 1/7411
137/550
(Continued)

FOREIGN PATENT DOCUMENTS

CN    101472626 A    12/2008
CN    100546554 C    10/2009
(Continued)

OTHER PUBLICATIONS

International Search Report and Written Opinion dated Feb. 16, 2018 in International Application No. PCT/EP2017/078068.
(Continued)

*Primary Examiner* — Scott J Medway
(74) *Attorney, Agent, or Firm* — Muncy, Geissler, Olds & Lowe, P.C.

(57) ABSTRACT

The invention relates to an interchangeable insert (1) for an ophthalmological medical device (99) for aspiration of fluid, such as for discharging fluid as part of suction flushing during an ophthalmo-surgical intervention, such as a cataract operation. According to the invention, this occurs by means of a fluid region (10) for receiving the fluid to be suctioned and a negative pressure region (20), to which a negative pressure can be applied. The fluid region (10) and the negative pressure region (20) are hermetically separated from each other by an at least partially flexible membrane (13).

20 Claims, 6 Drawing Sheets

(52) U.S. Cl.
CPC .............. *A61M 2205/0216* (2013.01); *A61M 2205/123* (2013.01); *A61M 2205/126* (2013.01); *A61M 2205/128* (2013.01); *A61M 2205/3331* (2013.01); *A61M 2205/3379* (2013.01); *A61M 2206/20* (2013.01); *A61M 2210/0612* (2013.01)

(58) Field of Classification Search
CPC .. A61M 2205/3331; A61M 2210/0612; A61M 1/77; A61M 1/92; A61M 1/0058
See application file for complete search history.

(56) References Cited

U.S. PATENT DOCUMENTS

| | | | |
|---|---|---|---|
| 4,976,162 A | 12/1990 | Kamen | |
| 5,125,891 A | 6/1992 | Hossain et al. | |
| 5,354,268 A * | 10/1994 | Peterson | G05D 16/2095 604/35 |
| 5,392,653 A * | 2/1995 | Zanger | G01L 9/14 73/756 |
| 5,423,738 A * | 6/1995 | Robinson | A61M 1/784 604/6.11 |
| 5,499,969 A | 3/1996 | Beuchat et al. | |
| 5,746,719 A | 5/1998 | Farra | |
| 6,036,458 A * | 3/2000 | Cole | A61M 1/0058 417/477.2 |
| 6,293,926 B1 * | 9/2001 | Sorensen | A61M 1/0058 604/153 |
| 6,511,454 B1 * | 1/2003 | Nakao | A61M 1/0062 604/131 |
| 8,197,231 B2 | 6/2012 | Orr | |
| 10,646,631 B2 * | 5/2020 | Günther | A61M 1/1601 |
| 2003/0108429 A1 * | 6/2003 | Angelini | A61M 1/0058 417/3 |
| 2003/0202894 A1 | 10/2003 | Leukanech et al. | |
| 2004/0059284 A1 | 3/2004 | Nash et al. | |
| 2004/0074281 A1 * | 4/2004 | Lobdell | A61M 1/73 73/1.57 |
| 2006/0224107 A1 * | 10/2006 | Claus | A61F 9/00745 604/44 |
| 2007/0098578 A1 | 5/2007 | Morgan | |
| 2009/0158855 A1 * | 6/2009 | Holden | A61M 1/73 73/756 |
| 2009/0163852 A1 * | 6/2009 | Cull | A61M 1/743 604/31 |
| 2009/0247938 A1 * | 10/2009 | Buboltz | A61F 9/00736 604/31 |
| 2009/0306585 A1 * | 12/2009 | Pang | A61M 5/14276 604/67 |
| 2010/0249693 A1 | 9/2010 | Links | |
| 2011/0092896 A1 | 4/2011 | Kuebler et al. | |
| 2011/0202032 A1 * | 8/2011 | Shih | A61M 5/14276 604/500 |
| 2012/0232466 A1 | 9/2012 | Kuebler et al. | |
| 2013/0023821 A1 | 1/2013 | Khalil | |
| 2013/0030407 A1 * | 1/2013 | Bourne | A61F 9/00736 604/500 |
| 2013/0150776 A1 * | 6/2013 | Bohm | A61B 3/16 604/9 |
| 2013/0245543 A1 * | 9/2013 | Gerg | A61M 1/71 604/30 |
| 2013/0343936 A1 | 12/2013 | Gray | |
| 2014/0076058 A1 * | 3/2014 | Brugger | G01L 19/0023 73/723 |
| 2014/0276428 A1 | 9/2014 | Gray et al. | |
| 2015/0164690 A1 * | 6/2015 | Peterson | A61M 1/777 604/67 |
| 2015/0250939 A1 * | 9/2015 | Kuntz | A61M 1/77 604/28 |
| 2016/0089268 A1 | 3/2016 | Chon | |
| 2019/0255231 A1 * | 8/2019 | Koppel | A61F 9/00745 |

FOREIGN PATENT DOCUMENTS

| | | |
|---|---|---|
| CN | 105979979 A | 9/2016 |
| DE | 2030536 | 12/1971 |
| DE | 1728343 | 2/1972 |
| DE | 68928524 T2 | 6/1998 |
| DE | 69032869 T2 | 6/1999 |
| DE | 19852574 A1 | 5/2000 |
| DE | 102007042964 A1 | 3/2009 |
| DE | 102008026014 A1 | 12/2009 |
| DE | 102007031722 B4 | 6/2011 |
| DE | 202010010336 A1 | 9/2011 |
| DE | 102012018982 A1 | 3/2014 |
| DE | 102009049430 B4 | 7/2015 |
| DE | 202015006341 | 11/2015 |
| EP | 2227196 B1 | 9/2014 |
| EP | 3318290 A1 | 5/2018 |
| EP | 3344307 B1 | 7/2018 |
| JP | S59-502132 A | 12/1984 |
| JP | H05-168698 A | 7/1993 |
| JP | 2016086935 A | 5/2016 |
| KR | 20160000231 A | 1/2016 |
| WO | 1984002078 | 7/1984 |
| WO | 9318802 | 9/1993 |
| WO | 9318802 A1 | 9/1993 |
| WO | 2000025710 A1 | 5/2000 |
| WO | 2002056805 A2 | 7/2002 |
| WO | 2007143677 | 12/2007 |
| WO | 2010129128 A1 | 11/2010 |
| WO | 2015094736 | 6/2015 |

OTHER PUBLICATIONS

Infiniti, Vision System, Operator's manual, Alcon Laboratories, 15800 Alton Parkway, Irvine, CA, 92618-3818, US, Apr. 2010, (siehe Seite 2, Revision T).
"Worterbuch Der Industriellen Technik" Dr.-Ing Richard Ernst, Band II, Englisch-Deutsch, Oscar Brandsetter Verlag, Wiesbaden, 6. Auflage, 2000.
Wikipedia Artikel, "Diaphragm pump", vom 15. Apr. 2016.
Abstract, "Flussigkeitsverbrauch wahrend der Kataraktoperation mit zqei Phako-Systemen (Alcon Infinity und die AMO-Sovereign CASE-Technologie)", Klin Monbl Augenheilkd 2006; 223-V90, DOI: 10.1055/s-2006-947004, veroffentlicht 2006—Machine Translation.
Definition, "Pneumatik" aus dem Duden—Machine Translation.
Consolidated List—Konsolidierte Liste—Liste Recapitulative—EP 16196998.5.
Notice of Opposition—Einspruch gegen ein europaisches Patent—EP 16196998.5.

* cited by examiner

STERILE VENTURI ASPIRATION

This application is a 371 National Phase of PCT Application No. PCT/EP2017/078068, filed on Nov. 2, 2017; which claims priority to European Patent application 16196998.5 filed Nov. 3, 2016 and each of which is herein incorporated by reference in its entirety.

The invention relates to a replacement insert or a cassette for an ophthalmological medical device according to the preamble of claim 1 and to a corresponding device or system according to the preamble of claim 11, and to a corresponding aspiration method according to the preamble of claim 12.

In the case of surgeries performed on the eye, for example in the case of cataract, vitrectomy or glaucoma surgery, the surgical instrument with which the physician performs the surgical procedure on the eye itself is connected via a tube system to a medical device by means of which—amongst other things—what is known as a suction flushing is performed, especially in order to remove from the eye any particles accumulating during the surgery. Here, an aspiration, that is to say a suction, of the particles and of liquid is performed—usually with one or more hollow needles introduced into the eye. At the same time liquid, or what is known as irrigation liquid, is supplied by means of an infusion. Here, the eye pressure should be kept as constant as possible so as to prevent any shrinking or swelling of the eye. Documents WO 00/25710, WO 02/056805, DE 10 2012 018 982 or DE 198 52 574 describe examples of devices of this kind and examples of applications of these devices.

In ophthalmological suction flushings of this kind, two different approaches for aspiration are used primarily. On the one hand, suction is performed using a peristaltic pump, in which—in accordance with the mode of action thereof—a required volume flow amount is specified at the time of actuation. On the other hand, suction is performed in accordance with the Venturi principle, with a negative pressure of the suction being specified at the time of actuation. Accordingly, either ophthalmological devices according to the Venturi principle or devices according to the peristaltic principle are used. Each of these two principles has its own specific characteristics and advantages and disadvantages, for example in respect of ripple effects of the suction, behavior in relation to occlusions and clearing thereof, etc. Which of these principles is applied is dependent, for example, on the preferences of the surgeon and/or on the specific surgical procedure—or simply on the type of device available.

For example WO 2010/129128 or DE 10 2007 031 722 presents a device that works in accordance with the peristaltic principle, and US 2016/0089268 presents an application of the Venturi principle.

In the case of the Venturi principle a negative pressure is generated by means of a Venturi nozzle (in accordance with the Venturi principle) by means of an airflow (for example from a compressed air connection in the operating theater) in a cavity. This cavity is connected as necessary, for example via a valve, to the aspiration system coming from the eye and thus brings about the aspiration by the negative pressure.

An ophthalmological Venturi system according to the prior art, however, has a number of disadvantages. For example, the silencer necessary for the Venturi nozzle can be contaminated by any germs from the eye fluid, and these germs, viruses and/or bacteria can then be blown into the surrounding environment. This can occur not only if, for example, the filling level detection fails and the liquid overflows, but also with even the most minor of swirling.

Special, upstream filter systems, which must be changed regularly, are indeed known, however they cannot prevent all risks of infection. The fact that the aspirated liquid usually comes into contact only with interchangeable cassettes is also of little help here, since the Venturi nozzle, the silencer thereof, etc., are part of the device and not part of the interchangeable cassette.

If, in the case of a Venturi cassette of this kind from the prior art, the area provided for receiving liquid becomes full, the surgical procedure must be interrupted in order to remedy this problem, which constitutes a further disadvantage.

Another disadvantage in the prior art can be that, in the event of malfunctions of the Venturi nozzle, an enormous positive pressure can build up in the aspiration system which could transfer into the eye and in the worst case scenario could lead to an injection of non-sterile outside air into the eye.

The known solutions from the prior art are therefore in need of improvement in their known form.

It is an object of the present invention to provide a method which improves an ophthalmological aspiration. An improved ophthalmological aspiration method and the devices used for that purpose shall be provided. In particular, the above-mentioned disadvantages shall be remedied.

It is accordingly also an object of the present invention to improve the ophthalmological aspiration device, in particular the region of an ophthalmological device intended for the aspiration and/or the associated replacement part.

Here, it is in particular an object to provide a corresponding, improved cassette for an ophthalmological device. The corresponding provision of an ophthalmological device for use of a cassette of this kind may likewise be a further part of the object.

A more specific object here is also to provide a solution which has the properties and characteristics of a known Venturi system valued by some surgeons, but avoids or at least mitigates the disadvantages thereof.

These objects are achieved in accordance with the invention by the features of the independent claims and/or by features of the dependent claims or these solutions are developed further.

The present invention relates to a replacement insert for an ophthalmological medical device for the aspiration of liquid. This aspiration can be performed in particular within the scope of what is known as a suction flushing during an ophthalmic surgical intervention, for example during cataract or vitrectomy surgery. During this aspiration, liquid—with or without solid-body components, such as shattered lens parts or the like—is to be removed from the eye. The aspiration of the present invention should be realizable here in particular primarily in accordance with what is known in specialist circles as the "Venturi principle", that is to say in accordance with the principle of a suction by means of a pneumatic negative pressure and not only in accordance with a hydraulic volume delivery principle, as is attained, for example, with a peristaltic pump. In particular, the objective here is to attain suction characteristics similar or identical to conventional Venturi systems. Hereinafter, the term "clean Venturi replacement insert" will therefore also be used alternatively for the replacement insert.

The replacement insert according to the invention has a liquid region for receiving the liquid to be suctioned away, and a negative pressure region, which in particular is liquid-free and to which a pneumatic negative pressure can be applied. Here, the liquid region is hermetically separated from the negative pressure region by an at least partially flexible membrane.

In particular, the negative pressure region especially when the replacement part is inserted in the medical device—forms a hollow space. This hollow space contains a gas, in particular air or room air. The gas can be suctioned (at least in part) from this hollow by means of a corresponding suction arrangement so that a negative pressure in relation to the surrounding room air is created. In regular operation the negative pressure region therefore usually does not contain any liquid.

The membrane can be designed here for example as a thin, flexible film, for example as a plastic film or as a metal foil, or as a combination of the two. The membrane can be formed here for example from a polyamide (PA) and/or polypropylene (PP), wherein, depending on the material, an appropriate film thickness can be determined by way of calculation and/or tests in order to attain the required flexibility alongside stability. For example, the film is formed from a polyamide (PA) and/or polypropylene (PP). The film can be designed here with a thickness of approximately 40 to 100 μm, especially approximately 60 to 70 μm. Besides a film formed from a single material, the film can also be constructed from two materials, for example with a layer formed from PA approximately 20 μm thick and with a layer formed from PP 50 μm thick.

In one embodiment this flexible membrane can extend for example at least approximately over the entire area of a side wall of the liquid region. For example, this is achieved by way of a tray-like or shell-like hard shaped part which is closed on its open side by the membrane. Here, the shaped part and membrane form a hollow space of variable volume as at least part of the liquid region. The volume of the liquid region is variable here by at least partial deformation of the membrane, in particular also down to approximately zero.

In another embodiment this flexible membrane can be designed for example also only peripherally around a solid, for example plate-shaped element movable thereby. In other words, the membrane is generally designed and arranged in such a way as to create a movability (of at least a region) of one or more of the sides surrounding the liquid region. The flexible membrane is thus arranged and designed especially to vary the enclosed volume of the liquid region, especially in relation to a non-flexible basic form of the replacement part. The entire replacement part is preferably manufactured from one or more plastics, for example in order to simplify a potential recycling.

Alternatively, embodiments with a piston-cylinder arrangement, in which the cylinder forms the liquid region and the movable piston, instead of the membrane, is pneumatically actuated and used for pressure transfer, are also conceivable. A further alternative is one in which a piston or a rigid wall which is connected movably via a membrane is moved by means of a mechanically or magnetically applied force. The latter, however (at least without specific control technology), would go against the principle of the present invention, in accordance with which the characteristics of a Venturi system are to be maintained where possible.

In accordance with the invention the replacement insert can be designed here for example with a tray or half-shell, that is to say in particular a type of shell-like tray with a base and a peripheral upright edge. This half-shell can be formed for example from a plastic—for example a polypropylene (PP)—or a metal and/or a thermoplastic elastomer (TPE). In particular an injection-molded part, for example, made of a polyethylene or a polypropylene, lends itself for mass production. For example, the hard component of the half-shell can be formed from a polypropylene (PP), and the soft component can be formed from a TPE, preferably by means of injection molding. The membrane can then be connected to this half-shell—in a hermetically sealing manner. Here, the membrane can be formed for example as a thin, flexible film, in particular with a film thickness that is thin enough that the required flexibility is provided (at least partially at the points necessary for the volume change, or also over at least approximately the entire film face), but at the same time a sufficient tear strength is ensured. The film can be designed here in such a way that in its rest position it nestles as closely as possible against the inner form of the half-shell. This can be done by prior shaping or for example also during the production of the replacement insert. For example, the half-shell can be spanned by the film and peripherally sealed, bonded, welded, ultrasonically welded, pressed, sealed or clamped at the edge. The film can then be brought into the corresponding form for example by thermoforming into the form of the half-shell—especially in such a way that this thermoformed shaping then corresponds to the preferred rest position of the membrane.

A flexible film of this kind can be arranged here in particular in such a way that the liquid region is formed between an interior of the half-shell and an inner side of the flexible film. This liquid region—depending on its filling level—has a volume of at least approximately zero to approximately several ten to several hundred milliliters, for example 100 ml. Especially with the additional pump arrangement, the liquid volume can be smaller than without, for example with less than 500 ml, preferably approximately 100 ml.

Accordingly, part of the negative pressure region can be formed by an outer side—opposite the inner side—of the film. For example, an edge of the half-shell with inserted cassette, together with a counter piece in the device, can form a peripherally sealed chamber as negative pressure region, which is connected to an air suction system for providing the negative pressure. Here, as the replacement insert is inserted, a clamping in particular between the replacement insert and the counter piece can be provided, by means of which a closed volume is formed. For example with appropriate sealing elements on the replacement part and/or on the counter piece in the device, the negative pressure region can be formed as a closed volume (apart from the suction system), in particular a hermetically closed volume. Here, one embodiment of the replacement part according to the invention can be designed for example as a multi-component injection-molded part, in which the film is inserted or optionally also injection molded integrally. Attention is drawn here accordingly to the known possibility for combining the used materials in this method.

The replacement insert according to the invention can be designed in one embodiment for example as an interchangeable cassette for the ophthalmological medical device. Here, the liquid region is designed as a suction chamber hydrostatically connectable to an aspiration connection of a surgical instrument. This suction chamber is designed for the at least temporary, in particular direct intake of aspirated liquid and—as already described—is formed substantially with the flexible membrane and the solid half-shell. Here, the membrane—when the cassette is inserted in the medical device—can be acted on from outside with a negative pressure via the negative pressure region, so that the negative pressure can be transferred from the negative pressure region via the membrane to the liquid region, without the air suctioned from the negative pressure region being able to come into contact with the liquid. Here, in particular with appropriate design of the material and of the parameters, in particular the film thickness, of the membrane, the aspiration characteristic is the same as, or at least similar to that of known Venturi aspiration systems. In particular, the membrane can be a large-area membrane, which specifically can mean that the area of the membrane accounts for a significant proportion of the surface surrounding the liquid region. For example, the area of the membrane compared to the total surface of the liquid region might lie not only merely in a single-digit percentage range, but for example may account for more than 16%, in particular more than 25%, or more than 35%, or even more. With an accordingly dimensioned, large-area membrane, a characteristic particularly similar to a known Venturi system can be attained. In a specific embodiment the membrane area may optionally also account for up to approximately 100%, wherein however a percentage of less than 80% is preferably applied so that at least part of the surface of the liquid region is formed by the solid half-shelf.

The replacement insert according to the invention can also be designed in another embodiment as an optional auxiliary module, which can be attached to an ophthalmological basic cassette—which for example already comprises at least one peristaltic pump, connections or valves. For example, the optional auxiliary module and the basic cassette can be fixedly connectable to one another (for example can be snapped together, can be clamped together, can be locked together, etc.), so that, when the auxiliary module is attached, a hydraulic connection of the liquid region to an aspiration system of the basic cassette can be produced. The attachment can be performed before the cassette is inserted—that is to say for example at the time of the surgical procedure—by removing the basic cassette and as necessary the clean Venturi replacement insert from their sterile packaging and joining these together on site, preferably non-releasably. If the auxiliary module is already attached at the factory, a bonding, pressing, welding or form-fitting connection to the basic cassette can alternatively also be realized, and the resulting non-releasably connected replacement cassette with clean Venturi replacement insert according to the invention can be packaged together in a sterile manner, for example in a blister packaging. At the time of joining, a breakout part or seal of the basic cassette, for example, can be broken in order to provide a connection to the aspiration system thereof, or the basic cassette can have a valve or the like for releasing a connection of a liquid channel towards the clean Venturi replacement insert.

In the case of the replacement insert according to the invention, the negative pressure can be generated by an air suction arrangement in the medical device. For example, an electrically operated partial vacuum pump can be used, or also a Venturi nozzle or another air delivery arrangement, by means of which a negative pressure can be generated. (A partial vacuum is provided here, since, in accordance with the invention, a complete vacuum is not usually necessary, but instead only a sufficient negative pressure in relation to the atmospheric pressure). A vacuum pump usually offers the advantage of a quiet and low-maintenance operation and avoids problems of an undesirable positive pressure in the event of a blockage. In particular, the air suction arrangement can be designed here in such a way that the value of the generated negative pressure is adjustable or controllable. Typical value ranges for the negative pressure in the sense of the present invention are for example approximately from 0 to 850 mbar below atmospheric pressure. If a vacuum connection is provided in the operating theater, a connection thereto can also be produced optionally instead of a device-side air suction arrangement, or a pressure-vacuum conversion by means of Venturi nozzle can be realized.

Part of the vacuum arrangement, or a part functionally connected thereto, is formed in the device as a counter piece which, by means of an edge of the replacement part, in particular peripherally closes off the half-shell and/or the membrane in a sealed manner when the replacement part is inserted. Here, the negative pressure region is formed between the device and the replacement part. In particular, a seal can be provided here on the replacement part, especially on the edge thereof, and/or on the counter piece in the device, said seal for example comprising an elastomer, a thermoplastic elastomer, a silicone, or another known seal form. In particular, whilst the replacement part is being inserted or following the insertion thereof, a clamping force can be applied between the counter piece and the inserted replacement part, by means of which clamping force the seal provides its effect.

In the replacement insert according to the invention the liquid region may comprise a pressure detection arrangement or may be hydrostatically connected to an arrangement of this kind. This arrangement is designed in such a way as to detect a negative pressure and/or positive pressure (absolute pressure or preferably relative to the surrounding atmosphere) in the liquid region. Here, the pressure detection arrangement, besides a complete integration in the replacement insert, can also preferably be attached only partially thereto. For example, the replacement part can have just one pressure measuring membrane connected to the liquid region, and an associated measuring element, which determines a force or a deflection of the pressure measuring membrane, can be attached in the device. This measuring element can enter into a functional, in particular mechanical connection with the pressure measuring membrane when the replacement part is inserted. Similarly, a further pressure detection arrangement can also be provided additionally or alternatively for the negative pressure region, and can be associated accordingly with the device or the replacement part. A pressure detection arrangement of this kind can be used here amongst other things for a wide range of monitoring and safety or control functions.

At least one valve can be provided in the replacement insert according to the invention or in the cassette in a liquid path between the liquid region and a connection for an aspiration line. Said valve can be designed in particular in such a way that a cross-section of the liquid path can be varied therewith, that is to say for example can be released or closed, but optionally can also assume intermediate positions. For example, a valve of this kind can be embodied as a cross-sectional area of the liquid path, which cross-sectional area is at least partially elastic along its periphery. This elastic region can then be actuated by a tappet, a slide or the like, in such a way that the free cross-sectional area in the liquid path thus can be varied, in particular can be opened or closed.

The replacement insert or the cassette according to the invention may also comprise a pump apparatus, in particular a peristaltic pump or membrane pump. By means of this pump apparatus, for example liquid can be discharged from the liquid region into an interchangeable waste container or collection bag. This discharge can be performed for example when the liquid region is filled up to a specific maximum capacity, or optionally can also be performed continuously during the aspiration or during aspiration pauses, preferably automatically. To this end, the liquid connection of the aspiration connection can be separated from the liquid region, for example by means of a valve provided for this purpose, in order to prevent pressure changes of the aspiration system at the patient during the discharge. The liquid connection of this pump apparatus may optionally also be separable from the liquid region, for example by means of a further valve provided for this purpose. For example, a stationary engaged peristaltic pump, however, may optionally generally also act as a closed valve, in particular if at least one pump roller fully squeezes the pumping cross-section. The waste container may be, for example, an interchangeable bag or canister, which preferably can be attached externally of the device and/or the cassette. This can be achieved for example via a connection line provided for this purpose, or preferably without tube with a bag that can be attached directly to the cassette.

In the replacement insert according to the invention, liquid paths can be formed in such a way that, in particular by means of at least one valve provided for this purpose, it is possible to switch between an aspiration by means of the negative pressure transferred to the liquid region, or an alternative pump apparatus, in particular peristaltic pump, or also a combination of these in particular, two. The same pump apparatus with which liquid can also be discharged into the waste container as described above can be used here as the alternative pump apparatus. An alternative pump apparatus of this kind may optionally also be used as a fallback option, for example if the liquid region is full—however, a continuation of the aspiration is necessary. Also in the case of failure of one of the two aspiration systems, the other can preferably take over seamlessly. A further option is that a delivery volume and/or aspiration pressure boost is attained by means of a cooperation of the clean Venturi aspiration according to the invention and the pump apparatus, which can be helpful in certain situations during a surgical procedure. In a corresponding embodiment the operator can also thus switch without delay and preferably continuously between a peristaltic or Venturi aspiration or any combination of these two modes. A return flow function can also be provided with appropriate actuation, which would be more complex with a solution based purely on a Venturi principle. Besides the value of the negative pressure, an adaptation of the suction characteristics can also be attained by means of the design and/or a variation of the volume of the negative pressure region; for example, the behavior in the case of occlusions, etc. can be influenced. For example, a larger volume of the negative pressure region brings about a greater flexibility of the suction behavior. In an embodiment according to the invention, in particular in an embodiment with clean Venturi and also pump apparatus aspiration, a high dynamic of the aspiration, which in particular is also adjustable or adaptable during operation, can thus be attained. A variation of the dynamic behavior of the aspiration can be attained in accordance with the invention for example also by influencing the negative pressure, in particular in respect of its build-up over time.

The replacement insert according to the invention and/or the medical device with which this insert cooperates can also have at least one filling level sensor for the liquid region. This sensor can be designed in particular as a pressure sensor, or as a sensor for determining a position of the membrane. For example, the filling level sensor can be designed as a switch actuated by the membrane when the liquid region is filled. When the liquid region is full, either a request can be made to replace the replacement insert, or liquid can be discharged from the liquid region in the manner described above by means of a pump apparatus. A fully emptied liquid region of the replacement insert can be detected by an additional or the same filling level sensor, or can be detected for example by means of the pressure detection arrangement already mentioned further above.

A replacement part according to the invention or a cassette according to the invention may also comprise an air bubble detector. This can work amongst other things for example optically, especially on the basis of the different refraction of liquid and air. For example, a viewing window into the liquid channel can be provided on the cassette or on the replacement part, through which viewing window a device-side optical sensor detects any air bubbles that form.

The present invention also relates to a corresponding device or system for eye surgery comprising a receiving apparatus for receiving at least one of the embodiments of a replacement insert according to the invention or a cassette according to the invention, in particular as described herein.

Here, the device comprises an air suction arrangement, in particular a vacuum pump or part of a basic vacuum pump or a Venturi nozzle, for generating a negative pressure in the negative pressure region. In particular, an arrangement for pumping or suctioning air from the negative pressure region of the replacement insert, which negative pressure region is hermetically separated from the liquid region of the replacement insert, is thus provided. Here, the receiving device for the replacement insert can be designed in particular in such a way that—with the replacement insert received—a peripheral region of the replacement insert is releasably joined, in a hermetically sealed manner, to a corresponding counter piece of the receiving device in order to form the negative pressure region. The negative pressure region formed with the replacement insert and device can constitute in particular a volume region which is closed—apart from the air suction arrangement itself—and which also comprises an outer side of the membrane of the replacement part, which outer side in particular is accessible from outside. For example, a peripheral line or area can be formed here as sealing region, in particular with a seal, preferably with an elastomer or thermoplastic elastomer, on the replacement part and/or the corresponding counter piece on the device. The negative pressure region may for example additionally also comprise a leak sensor, for example by means of a liquid or moisture sensor and/or a pressure sensor, by means of which a malfunction or a defect of a seal, of the membrane, etc. can be detected indirectly or directly. The suction arrangement can be connected here in particular in the upper region of the negative pressure region, so that in the case of a leak no liquid can penetrate into the suction arrangement. The hydraulic connection from liquid region to the aspiration system can be provided here preferably in an upper region of the inserted replacement part, especially so as to thus prevent any air bubble formation, or so as to be able to easily discharge these air bubbles. The membrane is preferably designed in such a way that, in its rest position, especially after unpacking the replacement part, it keeps the volume of the liquid region at approximately zero. In particular, after the first insertion—that is to say at the time at which the replacement part is put into operation—what is known as a filling or flushing cycle can be run through, in which aspiration or preferably infusion liquid is firstly sucked into the liquid region and this liquid is then discharged, jointly with any air located in the aspiration system, from the replacement insert or the cassette and/or the tube system. For example, the discharge can be into a collection bag. This is advantageous in particular since an aspiration system filled entirely with liquid can react deterministically to pressure changes.

As described above the replacement part is put into operation or what is known as a filling or flushing cycle is performed here generally without a connection to a patient, for example as a preparatory measure by support staff. The aspirated infusion liquid can originate here for example directly from an infusion bag or an infusion bottle, especially from that which is also used for irrigation during a surgical procedure. During a surgical procedure, a contaminated aspiration liquid from the patient may be aspirated from the eye and must not come into contact with a successive patient, the ambient air or the device, in order to ensure sufficient sterility.

In one embodiment of the invention the flexible membrane may preferably be substantially inelastic, in particular in such a way that, in the application according to the invention, no (or only a negligibly small) elastic deformation of the membrane occurs within the intended working region of the cassette, for example by a corresponding material selection and dimensioning of the membrane. A substantially non-elastic membrane of this kind can prevent a falsification of the aspiration pressure caused by a force necessary for an elastic deformation of an elastic membrane, which for example can simplify an aspiration pressure control.

Similarly, the invention also relates to an aspiration method for an ophthalmological device, in particular an aspiration method according to a Venturi principle working on the basis of negative pressure. This method can be performed in particular within the scope of a suction flushing during cataract surgery, for example during a phacoemulsification or vitrectomy. The method according to the invention is performed here with a step of providing a hermetically closed liquid region, which is formed at least in part by a flexible membrane, and which liquid region is situated in a replacement insert the ophthalmological device and can be hydraulically connected to an aspiration connection to the patient.

The aspiration is performed here at least partially with a suctioning or pumping of air from a negative pressure region formed opposite the liquid region on an outer side of the membrane. Here, the pneumatic negative pressure in the negative pressure region is transferred by means of the membrane to a hydraulic negative pressure in the liquid region. Here, the negative pressure region can be formed by joining the replacement part to a device-side counter piece in a hermetically sealed manner, wherein the counter piece is designed with or connected to an arrangement for generating the negative pressure.

In other words, the method is an aspiration method for an ophthalmological surgical procedure according to the Venturi principle, in particular in a phaco device. In this case, a liquid region for the aspirated liquid in accordance with the invention is hermetically separated from a negative pressure region connected to the room air. In accordance with the invention a pneumatic negative pressure is thus transferred to a hydraulic negative pressure of the aspiration system by flexible membrane. In particular, the negative pressure region can be designed with a defined minimum volume, and therefore, by the pneumatic effect thereof, a dynamic characteristic of the aspiration is realized, which can be advantageous compared to a rigid peristaltic aspiration.

The aspiration method according to the invention can be performed with a step of measuring the pressure in the liquid region and/or in the negative pressure region, in particular wherein the negative pressure and/or the valve actuation are/is controlled on that basis. The aspiration method according to the invention can also be performed with a step of switching between an aspiration by means of the pneumatic negative pressure, which acts on the liquid region, and/or by means of a hydraulic volume delivery, in particular by peristaltic pumping. In the aspiration method according to the invention, liquid can additionally be discharged from the liquid region into a waste container, in particular by peristaltic pumping. Here, the liquid region in particular can be emptied, preferably continuously, during aspiration pauses.

The method according to the invention and the device according to the invention will be described in greater detail hereinafter, purely by way of example, with reference to specific exemplary embodiments illustrated schematically in the drawings, wherein further advantages of the invention will also be discussed. the drawings specifically show.

The depictions in the figures are for illustration purposes only and, unless explicitly stated otherwise, are not to be regarded as true to scale. Identical or functionally similar features shall, as far as practicable, be consistently marked with the same reference numerals and, where appropriate, distinguished by a letter as an index. The presented diagrams show the basic technical structure, which can be supplemented or modified by a person skilled in the art according to general principles.

Figure 1:
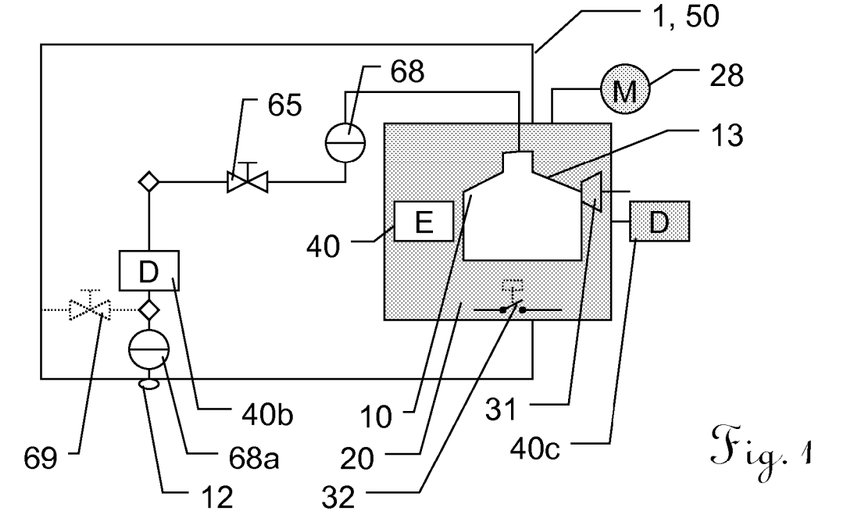
FIG. 1 a block diagram of a first embodiment of an example of a replacement part insert according to the invention.

FIG. 1 shows an embodiment of an aspiration method or a corresponding replacement insert 1 according to the invention in the form of a simplified block diagram. The following description follows the path of the aspirated liquid, wherein—in particular optional—elements within the sense of the invention can be varied also in respect of their order.

The aspiration connection 12 is provided for connection to an ophthalmic surgical instrument, for example a phaco handpiece, from which aspiration is to be performed, as interface of the replacement insert 1, which can also be designed as an interchangeable cassette 50 for an ophthalmological device. In the example shown here an optional air detector 68a, by means of which any air bubbles in the aspiration system can be determined, is situated in the aspiration line within the cassette. In this exemplary embodiment, infusion liquid can be guided into the aspiration system by means of the optional valve 69, for example in order to fill the cassette 50 with liquid at the time at which the cassette is put into operation and/or in order to reduce negative pressure in the case of occlusions in the aspiration system. Furthermore, the aspiration system comprises a pressure sensor 40b, by means of which the aspiration pressure can be monitored, in particular as negative and positive pressure in relation to the atmosphere.

The application requires the valve 65, by means of which the aspiration can be switched on and off or can be controlled. The optional pressure sensor 40 shown here can be used to measure, monitor and/or control the aspiration negative pressure, and/or to monitor the filling level of the liquid region 10. If the liquid region 10 is full or in the event of a malfunction, no negative pressure can influence the aspiration system, for example in spite of negative pressure in the negative pressure region 20.

An air detector 68 may likewise optionally also be provided. The aspirated liquid then passes into the liquid region 10 of the replacement part, which comprises a flexible membrane 13. This flexible membrane 13 is arranged at least partially in a negative pressure region 20, which is hermetically separated from the liquid region. In the event of an error caused by a leak of the liquid region 10, the negative pressure region 20 can be equipped with an optional moisture detector 32. The negative pressure region 20 or the liquid region 10 can also be equipped with an optional filling level sensor 31 for the liquid region 10. The negative pressure region 20 is acted on here by a negative pressure which is generated by discharging the air present in the negative pressure region 20, for example by a gas delivery arrangement 28 such as the shown (partial) vacuum pump 28, or another, equivalent arrangement. A pressure sensor 40c for measuring, monitoring and/or controlling the negative pressure generated by the gas delivery arrangement 28 can optionally be provided, and in particular the negative pressure can thus be adjustable and/or controllable.

At the time of construction, parts of the elements required in order to attain the above-mentioned functionalities can also be arranged at least in part in the device in which the replacement part 1 is inserted for operation thereof. In particular, these may be the active parts of the actuators or sensors, which cooperate with the cassette. However, in accordance with the purpose of the replacement part, all regions coming into contact with the liquid during regular operation are to be arranged in the cassette (or outside the device). The cassette therefore preferably contains, where possible, only the passive parts of these elements. In accordance with the invention, in particular actuation elements for the valves 65, measurement electronics for the sensors 40, 40b, 40c, 68, 31, 32, the gas delivery arrangement 28, etc. can be arranged in the device in which the replacement part is inserted. In particular, at least part of the negative pressure region 20 can also be formed by a device-side counter piece for the cassette 50. By way of example, blocks within the device are preferably shown highlighted in the diagram, wherein this corresponds only to a possible embodiment and should not necessarily be considered to be limiting.

Based on some of the advantages mentioned further above compared to the known ophthalmological Venturi aspiration solutions from the prior art, the present invention can also be referred to as a "clean Venturi", since it provides the behavior of a conventional Venturi system without the above-mentioned disadvantages, in particular without the problems concerning contamination.

Figure 2:
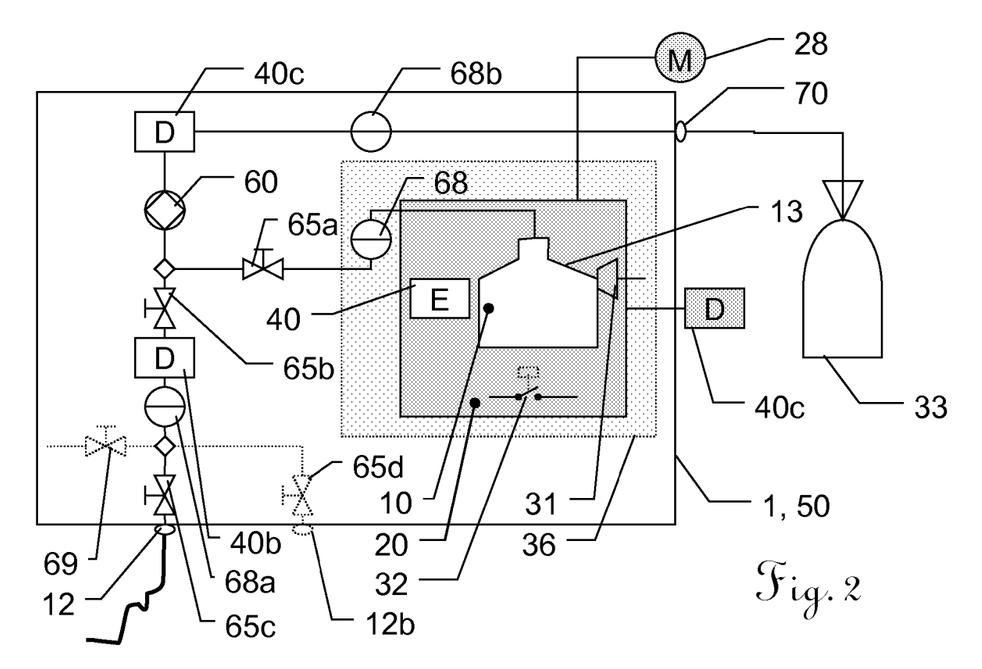
FIG. 2 a block diagram of a second embodiment of an example of a replacement insert according to the invention.

FIG. 2 shows an embodiment of a clean Venturi aspiration according to the invention or a corresponding ophthalmological cassette 50 in the form of a simplified block diagram. The figure primarily constitutes an extension of the above-mentioned functionality, and therefore elements that remain the same will not be discussed again specifically, and instead reference should be made to the description above. Specifically, in this extended embodiment according to the invention of the ophthalmological cassette 50, an additional pump arrangement 60, for example a Venturi or membrane pump, is added in the aspiration system. In the shown embodiment an additional valve 65b and an optional air bubble detector 68b are also shown. By means of these elements, in addition to the aspiration explained for FIG. 1, liquid can be discharged from the liquid region 10, to an outlet 70 of the cassette 50, where a disposable waste bag 33 can be attached. The liquid region 10 can thus be emptied again, and the cassette 50 does not necessarily need to be exchanged when the liquid region 10 is full. Furthermore detailed application possibilities according to the invention of this additional pump arrangement 60 will be described hereinafter. An optional second aspiration connection 12b and valves 65c and 65d functionally necessary therefor are also shown. This embodiment of a cassette 50 can also be formed for example by supplementing a basic cassette, which already comprises the additional pump arrangement 60, as necessary for a clean Venturi replacement part according to the invention, which is denoted here by way of example by the region 36. The basic cassette more specifically can be designed as in EP16197018, which was filed on the same date by the same applicant and which is incorporated herein by reference.

Figure 3:
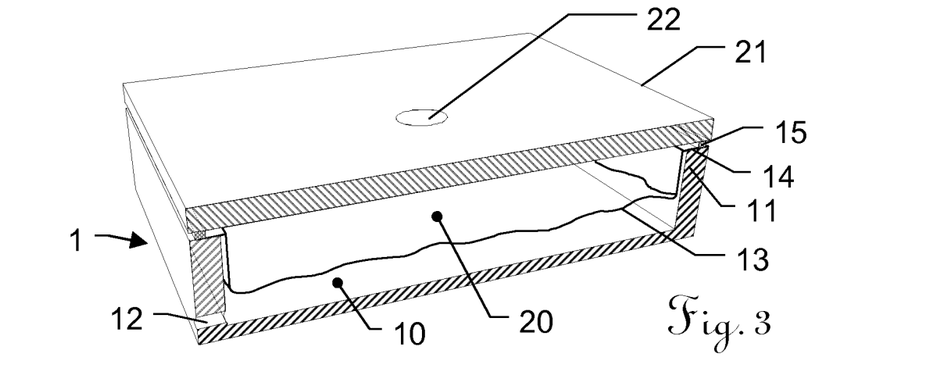
FIG. 3 a sectional depiction of an example of a replacement insert according to the invention.

FIG. 3 shows an exemplary, simplified illustration of a replacement part 1 according to the invention in a sectional depiction. What is shown therein is the tray or half-shell 11, which is rigid, for example is formed from a rigid material, such as an above-mentioned hard plastic or metal. A possible example of a material that can be used specifically for an embodiment is, for example, a polypropylene permitted for medical applications, or another comparable hard plastic material which satisfies the properties essential for this application, in particular for example with a bending modulus for example of approximately 800 MPa or more. This tray 11 can be produced preferably for example by means of injection molding or thermoforming/deep drawing. The half-shell forms part of the liquid region 10, which can be connected via the connection 12 to the ophthalmological aspiration system. The membrane 13, which on an inner of its flat sides forms a further part of the liquid region 10, is connected to the half-shell 11 in a hermetically sealed manner. The membrane 13 is formed here in particular as a film. For example, it is formed from one of the above-mentioned plastics and/or with a metal foil in such a way that it is flexible, especially since it has an appropriate, low thickness or wall thickness, adapted to the material. A thickness of less than 1 mm, for example a thickness of 0.06 mm, with the use of polyamide (PA) and/or polypropylene (PP) is preferable. In one embodiment the film can also be formed from a plurality of materials, for example with a layer formed from PA approximately 20 μm thick and a layer formed from PP approximately 50 μm thick. The advantages of the materials can thus be combined, for example the PP layer can have advantages in respect of the weldability to the half-shell 11, in particular if the latter is likewise formed from PP. Accordingly, the film 13 can thus be constructed on the inner side of the liquid region 10 from the same material as the half-shell 11 or a compatible material. The outer side of the membrane 13 can consist for example of a material having other advantages, for example in respect of tear strength, barrier properties, sealing properties, flexibility, etc. In the above-mentioned example the film is formed for example from PA, but could also be formed from other materials, for example aluminum.

The hermetic sealing of the half-shell 11 and membrane 13 can be achieved for example by welding, ultrasonic welding, bonding, pressing, clamping, by insertion of the membrane 13 in an injection mold, multi-component injection molding, etc. In the shown example this is achieved on the sealing shoulder 14.

On the outer side of the membrane 13, opposite the liquid region 10, there is provided the negative pressure region 20. This is at least partially open when the replacement part 1 is not inserted, such that there is (at least pneumatic) access to the membrane from this side. In particular, in one embodiment the membrane 13 of the replacement part 1 can be openly accessible when the replacement part is not in the inserted state, but alternatively, in another embodiment the replacement part 1 can also have a cover in the negative pressure region 20, which cover hermetically closes the negative pressure region 20 apart from an air connection 22 for introducing the negative pressure. In particular in the embodiment without cover at the replacement part 1, part of the negative pressure region 20 is formed by a counter piece 21 situated in the device. This counter piece 21 is pneumatically connected to an arrangement (not shown here) for generating a negative pressure, likewise situated in the device. In the simplified sketch shown here, this counter piece 21 is illustrated as a plate which—when the replacement part 1 is inserted in the device—is brought into abutment against the negative pressure side of the replacement part via a seal 15 arranged in-between. In any case, apart from the arrangement for generating the negative pressure, a volume closed off, in particular hermetically, is thus formed as negative pressure region 20 and can be acted on by the negative pressure for aspiration.

In another embodiment according to the invention the counter piece 21—when performing the aforementioned function—can deviate from the plate form shown here, for example can be formed as a cavity, half-shell, etc. The seal 15 can be associated here with the replacement part 1 or the counter piece 21 or also both of them. The seal 15 is preferably associated with the replacement part 1, since it is then replaced together with the replacement part 1, and therefore cannot become worn over time.

In another embodiment according to the invention the counter piece 21 can also be designed as a half-shell or cavity, and the replacement part 1 can be formed substantially flat or likewise as a half-shell. One practical embodiment for example could thus also be constructed conversely. For example it could be constructed with a cavity in the device 99, which cavity, when the replacement insert 1 is inserted, comes to rest, in a manner providing a hermetic seal in relation to the room air, over a liquid region 10 of the replacement insert 1, which liquid region is formed by the membrane 13 in the form of a flexible bag. The bag forming the liquid region 10 comes to lie here in the negative pressure region 20, which is formed as a negative pressure chamber or suction chamber by the cavity in the device 99. Here, this bag can also be at least partially connected to the replacement part 1 or can be formed thereby.

Figure 4:
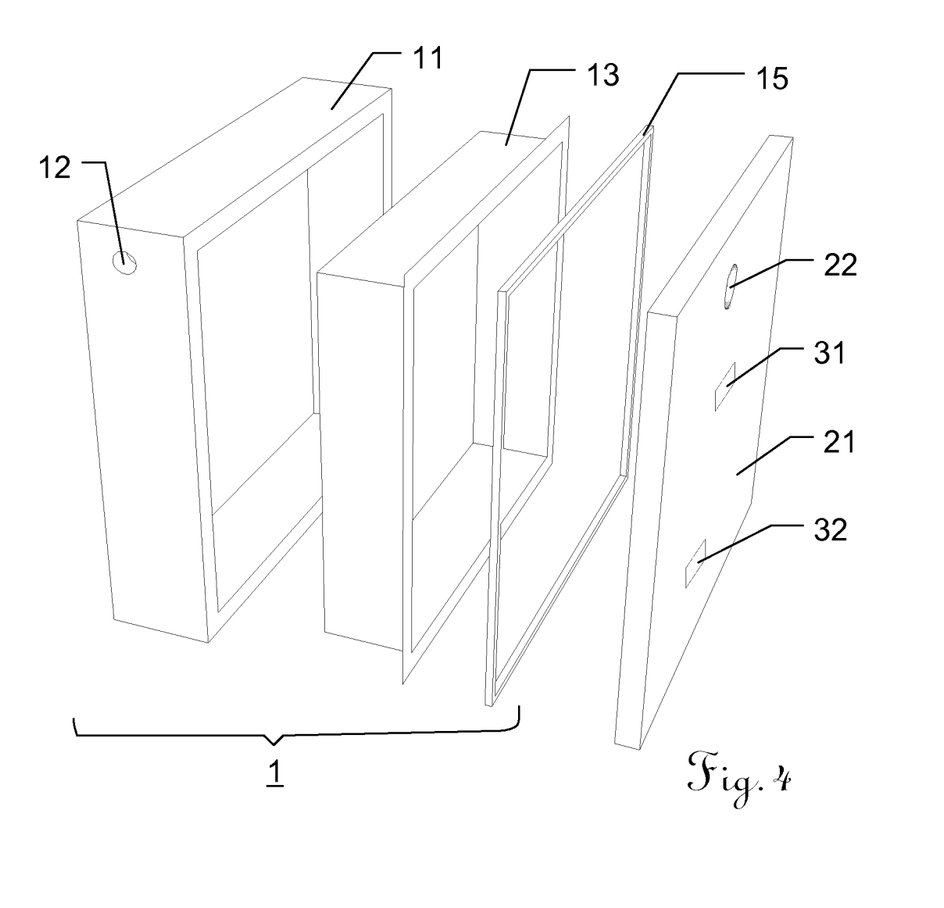
FIG. 4 an exploded depiction of an exemplary second embodiment according to the invention of a replacement insert.

FIG. 4 shows, by way of example, a simplified exploded illustration of a replacement part 1 and a device-side counter piece 21, wherein only the most essential elements from a functional viewpoint have been shown. The solid tray 11 forms a carrier of the replacement part 1, which is handled and inserted into an ophthalmological device. The flexible film 13 is fixedly connected peripherally to the tray 11, in particular in an air-tight and moisture-tight manner.

The seal 15 is preferably also part of the replacement part 1 and in particular is fixedly connected thereto. The seal is arranged in such a way that it runs in an encircling manner on the negative pressure side of the film 13, in particular in such a way that a hermetically closed negative pressure region can be formed on the replacement part side via the seal.

The insertion can be performed for example in the shown upright orientation, that is to say for example to the rear in the illustration, in a slot in the device, in which the replacement part 1 is then clamped in the device from the side, i.e. for example in this illustration from the right-hand side, with the device-side counter piece 21 in such a way that the seal 15 performs its function. In an alternative embodiment the replacement part 1 could also be inserted flat with the membrane side towards the device, so that the seal 15 terminates with the device-side counter piece 25—in other words the device is thus arranged to the right in the shown illustration, wherein here only the counter piece 21 as part of the device is shown. The device may optionally also have a filling level sensor 31 for the liquid region and/or a moisture sensor 32 for the detection of leaks, preferably in the negative pressure region.

Figure 5A:
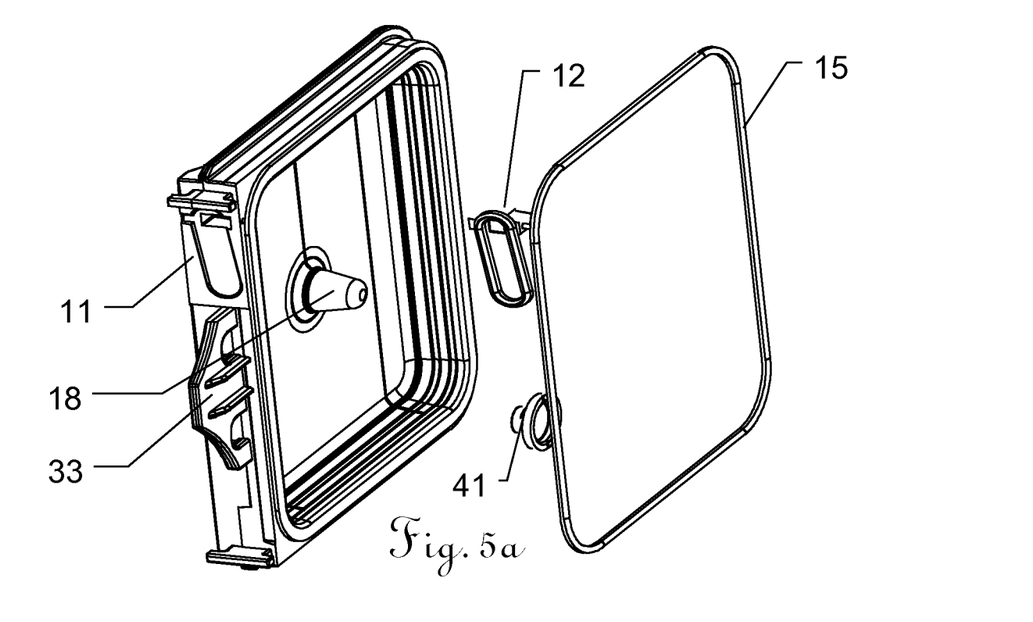
FIG. 5a shows a first depiction of an exemplary third embodiment according to the invention of a replacement insert in a multi-component injection-molded design.

FIG. 5a shows a possible structural embodiment of a replacement part 1 according to the invention. The tray 11 is shown as an injection-molded part formed from a hard plastic. At least parts of the inner cavity of this tray 11 form here, together with the membrane 13, the liquid region 10. The replacement part has externally a tab 33 for handling and/or for securing to a basic cassette. In this embodiment, in the middle of the tray 11 there is formed a dome-shaped protuberance 18, by means of which for example an improved dimensional stability and/or an advantageous deformation behavior for the membrane 13 (not shown here) in the event of volume changes to the liquid region can be attained. For the sake of clarity, the seal elements preferably formed from an elastomer or thermoplastic elastomer for the aspiration connection 12, and for the counter piece 21 (not shown here), and a measuring membrane 41 for a pressure measuring arrangement in the liquid region are shown. An example of a specific material for a possible embodiment is for example a thermoplastic elastomer or elastoplast permitted for medical applications, or another soft plastic material comparable in respect of its properties essential for this application, in particular for example with a Shore A hardness of approximately 20 to 100.

Figure 5B:
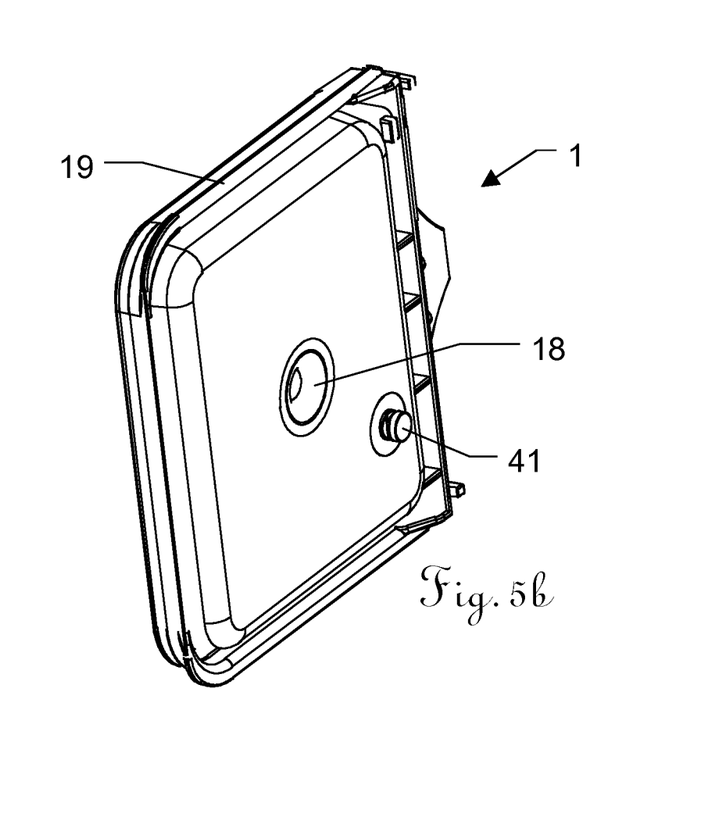
FIG. 5b shows a second depiction of the exemplary embodiment of a replacement insert according to the invention in a multi-component injection-molded design.

FIG. 5b shows the above exemplary embodiment of the replacement part 1 according to the invention from the other side. The protuberance 18 forms an indentation here accordingly, which for example can be used to center the replacement part 1 in the device. A guide web 19 is also situated at the top and bottom in this example, in order to facilitate the insertion of the replacement insert 1 into the device. The part 41 for the pressure measuring arrangement accessible from outside is also shown.

Figure 6A:
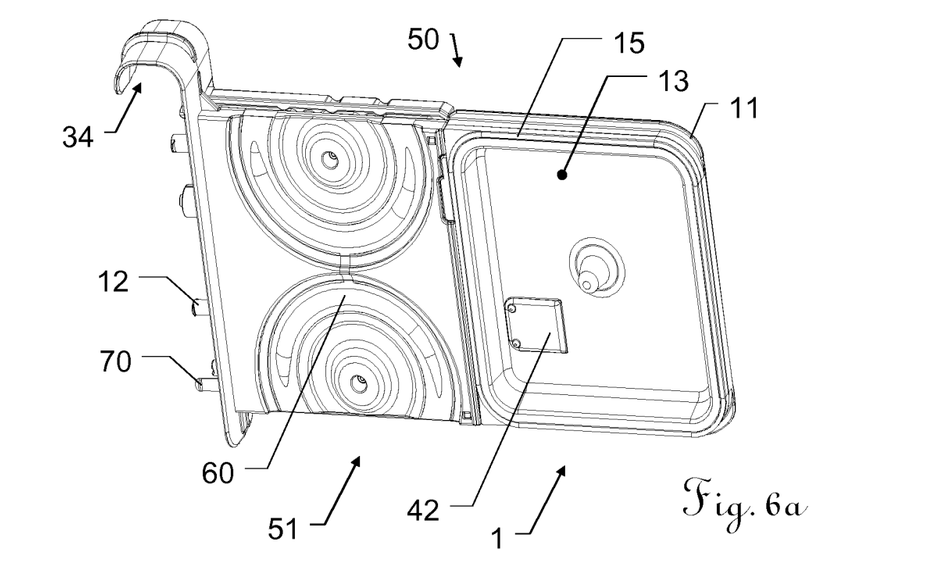
FIG. 6a shows a first depiction of a first exemplary embodiment of an ophthalmological cassette according to the invention with replacement insert according to the invention.

In FIG. 6a a further exemplary embodiment of a replacement insert 1 according to the invention is shown, which is designed as part of an ophthalmological cassette 50 which is interchangeable as a whole, that is to say especially in conjunction with a basic cassette 51 with further functionalities. In the embodiment before, the replacement insert 1 was designed per se as an ophthalmological cassette 50 of this kind, but had fewer functionalities than the example presented now.

The half-shell 11 or Venturi tray 11, seal 15 and film 13 as separation between liquid region 10 and negative pressure region 20 have already been described and can be embodied here analogously or similarly. A fixed covering 42 above the pressure measuring membrane 41 is shown here in the liquid region 10, in order to prevent contact with the membrane 13 of the Venturi tray 11, since this could hinder a pressure measurement. The liquid region 10 of the Venturi tray is hydraulically connected to the aspiration connection 12 on the front of the cassette 50, this being accessible in the inserted state. The holding hook or handle 34 is designed here in particular for one-handed insertion. Additionally shown here is an optional additional pump arrangement 60, which in the shown example is designed as a peristaltic pump, but for example can also be another pump arrangement, such as a membrane pump. What is denoted in particular is a flexible liquid channel portion in the cassette 50, by means of which a squeeze pump effect can be attained by rollers (not shown here) in the device. This additional pump arrangement is hydraulically connected to the aspiration liquid system, that is to say in particular to the liquid region 10. As a further partial aspect according to the invention, liquid (or also any air) can be delivered from the liquid region to a waste connection by means of this additional pump arrangement 60. For example, a bag for receiving the aspirated liquid can be connected to this waste connection, which bag can then be disposed of. With this aspect a filling level in the liquid region 10 can be reduced, preferably the entire liquid region 10 can be emptied at least approximately. This can take place in accordance with the invention during the surgical procedure, during short pauses in the surgical procedure, or outside the surgical procedure time. This additional pump arrangement 60 can also be used as a fallback option should the clean Venturi system according to the invention fail. In accordance with the invention a combined application of clean Venturi system and additional pump arrangement 60 is possible, in particular with flowing or abrupt transition or as permanent combined application. The additional pump arrangement 60 can also be used as an additional aspiration pressure or aspiration volume boost, for example in order to provide an increase in the aspiration delivery in the event of occlusions. A temporary return of liquid in order to remove occlusions can also be used with the additional pump arrangement 60. A complete emptying of the liquid region 10 can also be detected for example in that the negative pressure in the aspiration system (for example detected by means of the pressure measuring arrangement 40) then rises rapidly. In order to ensure a gentle pressure increase for a renewed activation of the aspiration from the patient, a short return of the emptying arrangement can be applied in order to reduce this increased negative pressure.

Figure 6B:
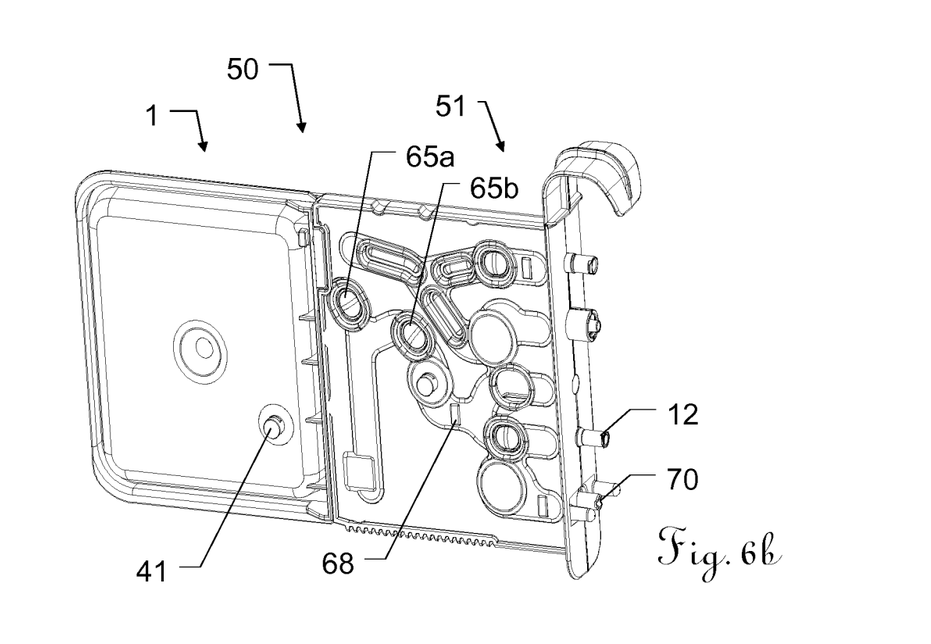
FIG. 6b shows a second depiction of the first exemplary embodiment of an ophthalmological cassette according to the invention with replacement insert according to the invention.

FIG. 6b shows the above, exemplary embodiment as seen from the other side. The denoted elements have already been explained. Additionally shown are the valves 65a or 65b in the aspiration liquid path, by means of which a flow cross-section can be varied, in particular can be closed or can be released. By means of these the aspiration into the liquid region can be switched or controlled. A connection or switchover in relation to the additional pump arrangement 60 can also be implemented thereby. An air bubble monitor 68, designed here with a viewing window in the cassette 50 for optical detection of air in the aspiration system, is also shown.

Figure 7:
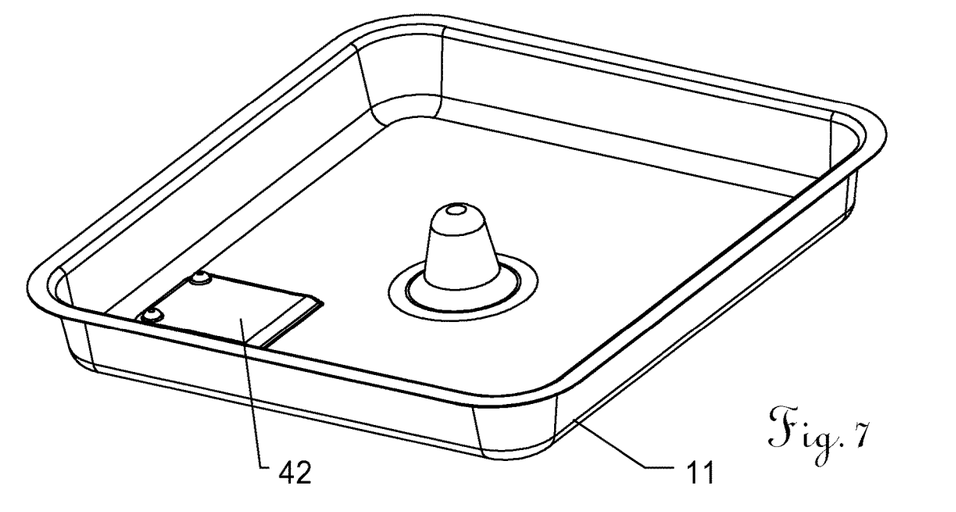
FIG. 7 shows a perspective depiction of an exemplary embodiment of a Venturi membrane of a replacement insert according to the invention.

FIG. 7 shows an example of an embodiment of a Venturi tray 11 according to the invention as a core piece of a replacement insert 1 according to the invention. An exemplary pressure sensor covering 42 can also be seen, as an embodiment for providing a pressure measuring arrangement by means of which for example a complete emptying of the liquid region 10 by an additional pump arrangement 60 can be determined on the basis of a rise of the detected negative pressure value in the liquid region 10, and/or by means of which a malfunction or a full liquid region can be determined on the basis of a drop of the negative pressure value in the liquid region 10.

Figure 8A:
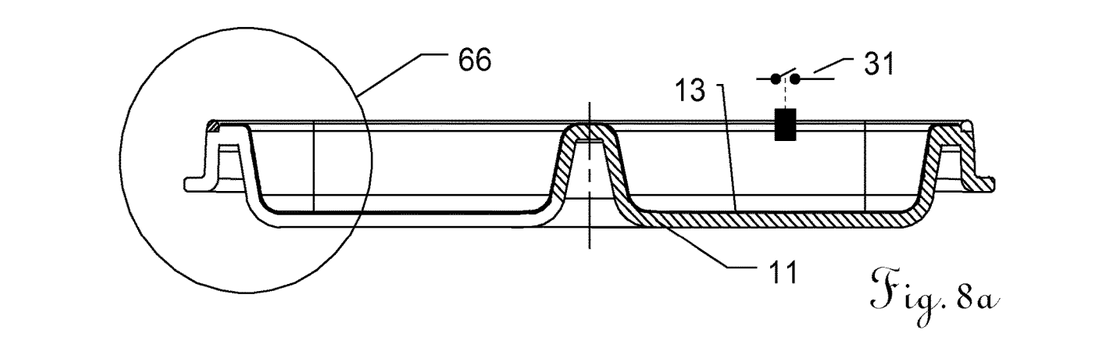
FIG. 8a shows a sectional depiction of an exemplary embodiment of a Venturi tray of a replacement insert according to the invention.
Figure 8B:
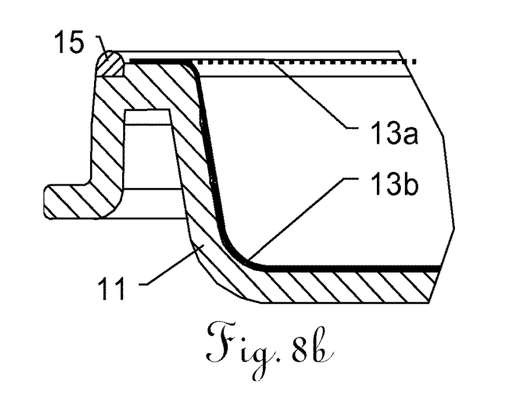
FIGS. 8b and 8c show a detailed depiction of an exemplary embodiment of a Venturi tray as half-shell of a replacement insert according to the invention.

FIG. 8a now illustrates, in a sectional depiction, an example in accordance with the invention of an embodiment of a Venturi tray 11 according to the invention as a core piece of a replacement insert 1 according to the invention. The thin membrane 13 embodied as a film is now also shown, in its position when the liquid region 10 is empty. The switch symbol symbolizes a device-side filling level monitoring of the liquid region 10, which for example can be implemented by a switch element actuated by the membrane 13. The detail 66 is shown again in FIG. 8b. Here, the membrane in the position 13a can represent the starting position in a first production step of the replacement insert. In a subsequent production step the membrane 13 can be thermoformed from position 13a to position 13b, preferably by introducing a negative pressure into the liquid region 10 via the aspiration connection thereof, optionally also with heating of the membrane 13. In particular, the membrane 13 can then remain in the position 13b as rest position, and the replacement insert can be provided in this form for first-time use. Alternatively, the membrane 13 could also be provided in a different position and, only when the device is put into operation, brought into the position 13b in the device, for example by means of the further pump arrangement 60, although this would usually be disadvantageous for example due to the time required.

Figure 8C:
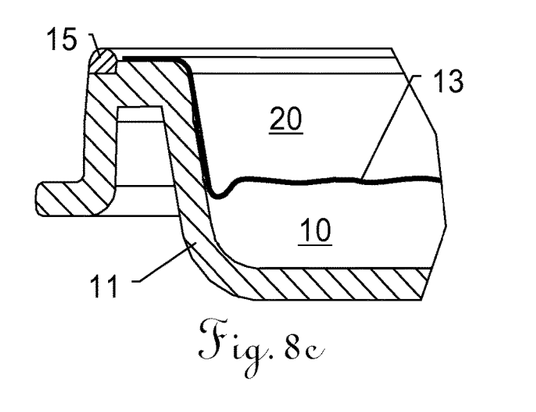

FIG. 8c shows detail 66 from FIG. 8a again, but with the membrane 13 in an intermediate position, for example during an aspiration, in which both liquid region 10 and negative pressure region 20 have a volume between their maximum and minimum values.

Figure 9:
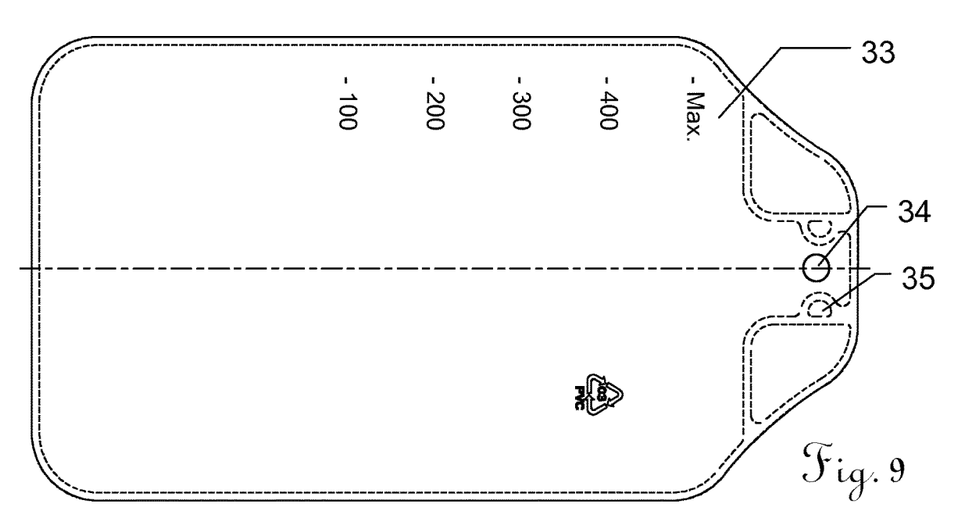
FIG. 9 shows a depiction of an exemplary embodiment of a waste bag according to the invention for a replacement insert according to the invention.

FIG. 9 shows an exemplary embodiment of a waste container 33, for example a waste sack or waste bag. It can be connected by means of its connection 34 to the waste connection 70 of the cassette, wherein this waste connection 70 is in particular mechanically and/or optically coded to prevent it from being confused with another connection of the cassette. Liquid from the liquid region 10 of the clean Venturi tray 10 can be discharged into the waste container 33 in accordance with one aspect of the invention. The waste container 33 can in particular have a special apparatus 35 for direct attachment to the cassette 50, and the cassette 50 can have the corresponding counterpart.

Figure 10:
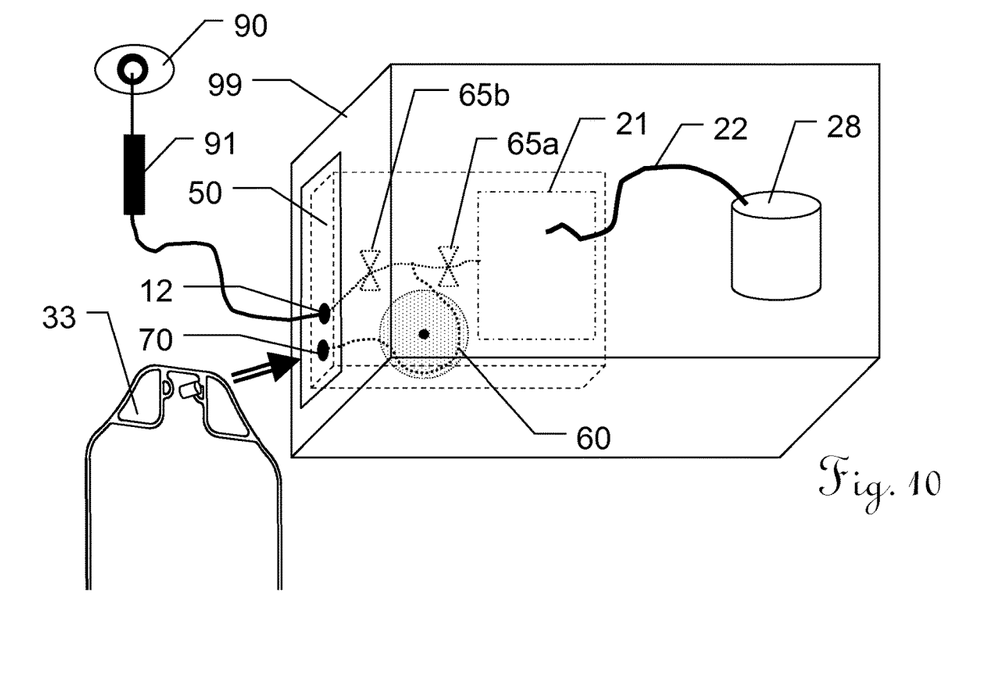
FIG. 10 shows a depiction of a detail of a device according to the invention with inserted cassette according to the invention and attached waste bag according to the invention.

FIG. 10 shows, by way of example, a detail of an exemplary embodiment of an ophthalmological device 99 according to the invention with an exemplary embodiment, received therein, of an ophthalmological cassette 50 according to the invention as an embodiment of a replacement insert 1 according to the invention. Reference is made to the above description for details of the cassette 50 and of the replacement insert 1. For example, a phaco handpiece 91 is connected to the aspiration connection 12 of the insert and can be used to perform a surgical procedure on the eye 90. This aspiration connection 12, as described, is connected in the cassette 50, in particular for example via at least some of valves, pressure sensors, air bubble detectors, additional pump arrangements, etc., to the liquid region of the replaceable insert (or the cassette)—which in this example is shown merely symbolically in its basic structure and in particular can be embodied in accordance with FIG. 1 and FIG. 2 and the associated description. By means of the additional pump arrangement 60 shown in this embodiment, liquid can also be discharged from the liquid region 10 into the waste bag 33 attached directly to the waste connection 70. The negative pressure region 20 is hermetically separated from the liquid region 10 by the membrane 13. This negative pressure region 20 is formed in this embodiment by the cassette 50 and the counter piece 21, and air can be suctioned from this negative pressure region 20, as shown for example in that the counter piece 21 is connected via the connection 22 to a vacuum pump 28. For the sake of clarity, further details of the device are not shown here.

The invention claimed is:

1. A replacement insert for an ophthalmological medical device for aspiration of a liquid, wherein the liquid is to be discharged within a scope of a suction flushing during an ophthalmic surgical intervention, the replacement insert comprising:
    a liquid region having a minimum volume of zero and a maximum volume of greater than 20 milliliters; and
    a negative pressure region, to which a pneumatic negative pressure is applicable,
    wherein the liquid region and the negative pressure region are hermetically separated from one another by at least partially a flexible membrane,
    wherein the replacement insert is designed in such a way as to suction the liquid into the liquid region by application of the pneumatic negative pressure,
    wherein the replacement insert is configured to allow for varying a volume of the liquid region for receiving aspirated liquid by at least partial deformation of the flexible membrane by the pneumatic negative pressure,
    wherein the pneumatic negative pressure in the negative pressure region is transferred by the flexible membrane to a hydraulic negative pressure in the liquid region, and the hydraulic negative pressure causes liquid to be aspirated into the liquid region, and
    wherein the liquid region forms a suction chamber for at least temporarily receiving the aspirated liquid.

2. The replacement insert according to claim 1, wherein the replacement insert is designed with a half-shell.

3. The replacement insert according to claim 1, wherein the replacement insert is designed as an interchangeable cassette for the ophthalmological medical device, wherein
    the liquid region is configured to be connected hydrostatically to an aspiration connection of a surgical instrument, and the liquid region is designed with
        the flexible membrane and
        a solid half-shell,
    wherein the membrane, when the cassette is inserted in the medical device, is configured to be acted on from outside by a negative pressure via the negative pressure region to cause a negative pressure transfer via the flexible membrane.

4. The replacement insert according to claim 1, wherein the replacement insert is designed as an auxiliary module, which can be attached to an ophthalmological basic cassette, which already comprises at least one peristaltic pump.

5. The replacement insert according to claim 1, wherein the pneumatic negative pressure is generated by an air suction arrangement in the medical device.

6. The replacement insert according to claim 1, wherein the liquid region comprises a pressure detection arrangement or the liquid region is hydrostatically connected to the pressure detection arrangement, the pressure detection arrangement being configured to detect a pressure level in the liquid region.

7. The replacement insert according to claim 1, wherein a valve is provided in the replacement insert in a liquid path between the liquid region and a connection for an aspiration line.

8. The replacement insert according to claim 1, wherein the replacement insert comprises a pump assembly.

9. The replacement insert according to claim 1, wherein liquid paths are formed in the replacement insert configured to switch on aspiration by means of at least one of:
    the pneumatic negative pressure transferred to the liquid region, or
    an alternative pump apparatus, or
    a combination of the two.

10. The replacement insert according to claim 1, wherein the replacement insert has a filling level sensor of the liquid region.

11. A device for eye surgery comprising a receiving apparatus for a replacement insert according to claim 1,
    wherein the device comprises an air suction arrangement for pumping air away from the negative pressure region of the replacement insert.

12. A method for aspirating a liquid by an ophthalmological device, comprising:
    providing a hermetically closed liquid region, which is formed at least in part by a flexible membrane, in a replacement insert for the ophthalmological device, the liquid region being configured to be hydraulically connected to an aspiration connection, and the liquid region having a minimum volume of zero and a maximum volume of greater than 20 milliliters; and
    suctioning air on a side arranged opposite the liquid region on an outer side of the membrane, wherein the outer side is part of a negative pressure region,
    wherein the liquid region is hermetically separated by the membrane from the negative pressure region and from surrounding room air,
    wherein a pneumatic negative pressure in the negative pressure region is transferred by the flexible membrane to a hydraulic negative pressure in the liquid region, and the hydraulic negative pressure causes liquid to be aspirated into the liquid region,
    wherein a volume of the liquid region for receiving aspirated liquid is varied by at least partial deformation of the flexible membrane by the pneumatic negative pressure, and
    wherein the liquid region forms a suction chamber for at least temporarily receiving the aspirated liquid.

13. The method according to claim 12, comprising at least one of:
    measuring a pressure level in the liquid region in order to identify a defect and/or a filling level in the liquid region; or
    detecting moisture or liquid in the negative pressure region in order to identify a defect of the membrane.

14. The method according to claim 12, further comprising switching on aspiration of the liquid by at least one of:
applying the pneumatic negative pressure, which acts via the membrane on the liquid region; or
applying a hydraulic volume delivery.

15. The method according to claim 12, further comprising discharging the aspirated liquid from the liquid region into a waste container.

16. The replacement insert according to claim 1, wherein an area of the membrane compared to an total surface of the liquid region accounts for more than 16%.

17. A method for providing an aspiration of liquids by an ophthalmological device by negative pressure suctioning, comprising:
providing a hermetically closed liquid region, which is formed at least in part by a flexible membrane, in a replacement insert for the ophthalmological device, the liquid region being configured to be hydraulically connected to an aspiration connection, and the liquid region having a minimum volume of zero and a maximum volume of greater than 20 milliliters; and
aspirating air on a side arranged opposite the liquid region on an outer side of the membrane, wherein the outer side is part of a negative pressure region,
wherein the liquid region is hermetically separated from the negative pressure region and from surrounding room air by the membrane,
wherein a pneumatic negative pressure in the negative pressure region is transferred by the membrane to a hydraulic negative pressure in the liquid region, and the hydraulic negative pressure causes a liquid to be aspirated into the liquid region,
wherein a volume of the liquid region for receiving aspirated liquid is varied by at least partial deformation of the flexible membrane by the pneumatic negative pressure, and
wherein the liquid region forms a suction chamber for at least temporarily receiving the aspirated liquid.

18. The replacement insert according to claim 1, wherein the maximum volume of the liquid region is less than 500 milliliters.

19. The method according to claim 12, wherein the maximum volume of the liquid region is less than 500 milliliters.

20. The method according to claim 17, wherein the maximum volume of the liquid region is less than 500 milliliters.

* * * * *